(12) United States Patent
Schneider

(10) Patent No.: US 11,458,690 B2
(45) Date of Patent: Oct. 4, 2022

(54) METHOD AND APPARATUS FOR BONDING SUBSTRATES

(71) Applicant: The Procter & Gamble Company, Cincinnati, OH (US)

(72) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 402 days.

(21) Appl. No.: 16/534,067

(22) Filed: Aug. 7, 2019

(65) Prior Publication Data

US 2020/0047420 A1    Feb. 13, 2020

Related U.S. Application Data

(60) Provisional application No. 62/718,071, filed on Aug. 13, 2018.

(51) Int. Cl.
*A61F 13/15*    (2006.01)
*A61F 13/49*    (2006.01)
(Continued)

(52) U.S. Cl.
CPC .... *B29C 65/4835* (2013.01); *A61F 13/15699* (2013.01); *A61F 13/15739* (2013.01); *A61F 13/49011* (2013.01); *A61F 13/49058* (2013.01); *A61F 13/4963* (2013.01); *B29C 66/0326* (2013.01); *B29C 66/7294* (2013.01); *A61F 2013/49092* (2013.01); *B29L 2031/4878* (2013.01)

(58) Field of Classification Search
None
See application file for complete search history.

(56) References Cited

U.S. PATENT DOCUMENTS 3,025,199 A    3/1962    Harwood
3,848,594 A    11/1974    Buell
(Continued)

FOREIGN PATENT DOCUMENTS

EP    2596778 A2    5/2013
WO    WO20150177603    11/2015

OTHER PUBLICATIONS

PCT International Search Report, dated Oct. 29, 2019, 12 pages.

*Primary Examiner* — Barbara J Musser
(74) *Attorney, Agent, or Firm* — Amanda Herman Berghauer; Charles R. Matson

(57) ABSTRACT

The present disclosure relates to methods for bonding first and second substrates together with tackifier free adhesives. The tackifier free adhesive may be applied to the second substrate to define an adherence zone. The first substrate is positioned on the adherence zone of the second substrate to define a first region and a second region of the adherence zone. In the first region, the tackifier free adhesive is positioned between the first substrate and the second substrate. In the second region, the tackifier free adhesive may or may not be positioned between the first substrate and the second substrate, and may not bond the first substrate with the second substrate. Thus, tackifier free adhesive may be applied to the second substrate to create an adherence zone defining a relatively large area that permits the placement of the first substrate thereon without the need to completely cover the adherence zone.

13 Claims, 13 Drawing Sheets

(51) Int. Cl.
*A61F 13/496* (2006.01)
*B29C 65/48* (2006.01)
*B29C 65/00* (2006.01)
*B29L 31/48* (2006.01)

(56) References Cited

U.S. PATENT DOCUMENTS

| | | |
|---|---|---|
| 3,860,003 A | 1/1975 | Buell |
| 4,107,364 A | 8/1978 | Sisson |
| 4,209,563 A | 6/1980 | Sisson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,556,146 A | 12/1985 | Swanson et al. |
| 4,576,600 A | 3/1986 | Joa |
| 4,589,876 A | 5/1986 | Van Tilburg |
| 4,610,678 A | 9/1986 | Weisman et al. |
| 4,662,875 A | 5/1987 | Hirotsu |
| 4,673,402 A | 6/1987 | Weisman |
| 4,687,478 A | 8/1987 | Van Tillburg |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany |
| 4,834,741 A | 5/1989 | Sabee |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz |
| 4,940,464 A | 7/1990 | Van Gompel et al. |
| 4,946,527 A | 8/1990 | Battrell |
| 4,950,264 A | 8/1990 | Osborn, III |
| 5,009,653 A | 4/1991 | Osborn, III |
| 5,025,910 A | 6/1991 | Lasure |
| 5,092,861 A | 3/1992 | Nomura |
| 5,151,092 A | 9/1992 | Buell |
| 5,167,897 A | 12/1992 | Weber et al. |
| 5,221,274 A | 6/1993 | Buell |
| 5,224,405 A | 7/1993 | Pohjola |
| 5,246,433 A | 9/1993 | Hasse |
| 5,267,992 A | 12/1993 | Van Tilburg |
| 5,360,420 A | 11/1994 | Cook et al. |
| 5,556,504 A | 9/1996 | Rajala |
| 5,569,234 A | 10/1996 | Buell |
| 5,599,335 A | 2/1997 | Goldman et al. |
| 5,628,097 A | 5/1997 | Benson et al. |
| 5,643,588 A | 7/1997 | Roe et al. |
| 5,674,216 A | 10/1997 | Buell et al. |
| 5,702,551 A | 12/1997 | Huber et al. |
| 5,735,840 A | 4/1998 | Kline |
| 5,897,545 A | 4/1999 | Kline |
| 5,916,661 A | 6/1999 | Benson et al. |
| 5,928,212 A | 7/1999 | Kline |
| 5,957,908 A | 9/1999 | Kline |
| 5,968,025 A | 10/1999 | Roe et al. |
| 6,004,893 A | 12/1999 | Van Tilburg |
| 6,107,537 A | 8/2000 | Elder et al. |
| 6,107,539 A | 8/2000 | Palumbo et al. |
| 6,116,317 A | 9/2000 | Tharpe, Jr. |
| 6,118,041 A | 9/2000 | Roe et al. |
| 6,120,487 A | 9/2000 | Ashton |
| 6,120,489 A | 9/2000 | Johnson |
| 6,153,209 A | 11/2000 | Vega et al. |
| 6,251,097 B1 | 6/2001 | Kline |
| 6,319,347 B1 | 11/2001 | Rajala |
| 6,410,129 B2 | 6/2002 | Zhang et al. |
| 6,426,444 B2 | 7/2002 | Roe et al. |
| 6,432,098 B1 | 8/2002 | Kline et al. |
| 6,450,321 B1 | 9/2002 | Blumenthal |
| 6,494,244 B2 | 12/2002 | Parrish |
| 6,524,423 B1 | 2/2003 | Hilt |
| 6,545,197 B1 | 4/2003 | Muller et al. |
| 6,550,517 B1 | 4/2003 | Hilt |
| 6,586,652 B1 | 7/2003 | Roe et al. |
| 6,604,623 B2 | 8/2003 | Sumi |
| 6,617,016 B2 | 9/2003 | Zhang et al. |
| 6,627,787 B1 | 9/2003 | Roe et al. |
| 6,649,010 B2 | 11/2003 | Parrish |
| 6,669,618 B2 | 12/2003 | Reising |
| 6,722,494 B2 | 4/2004 | Nakakado |
| 6,825,393 B2 | 11/2004 | Roe et al. |
| 6,861,571 B1 | 3/2005 | Roe et al. |
| 7,341,087 B2 | 3/2008 | Tabor |
| 7,371,302 B2 | 5/2008 | Miyamoto |
| 7,452,436 B2 | 11/2008 | Andrews |
| 7,569,039 B2 | 8/2009 | Matsuda et al. |
| 7,640,962 B2 | 1/2010 | Meyer |
| 7,650,984 B2 | 1/2010 | Giuliani |
| 7,770,712 B2 | 8/2010 | Mccabe |
| 7,811,403 B2 | 10/2010 | Andrews |
| 8,186,296 B2 | 5/2012 | Brown et al. |
| 8,720,666 B2 | 5/2014 | Papsdorf |
| 9,168,182 B2 | 10/2015 | Hargett |
| 9,248,054 B2 | 2/2016 | Brown et al. |
| 9,265,672 B2 | 2/2016 | Brown et al. |
| 9,730,839 B2 | 8/2017 | Brown |
| 9,737,442 B2 | 8/2017 | Findley |
| 2003/0233082 A1 | 12/2003 | Kline |
| 2004/0097895 A1 | 5/2004 | Busam et al. |
| 2004/0158212 A1 | 8/2004 | Ponomarenko et al. |
| 2005/0107764 A1 | 5/2005 | Matsuda et al. |
| 2007/0078427 A1 | 4/2007 | Raycheck |
| 2007/0093769 A1 | 4/2007 | Kline |
| 2009/0294044 A1 | 12/2009 | Gill |
| 2009/0312730 A1 | 12/2009 | Lavon et al. |
| 2012/0061015 A1 | 3/2012 | Lavon et al. |
| 2012/0061016 A1 | 3/2012 | Lavon et al. |
| 2013/0072887 A1 | 3/2013 | Lavon |
| 2013/0126071 A1* | 5/2013 | Shin .............. B65H 35/006 156/60 |
| 2013/0211356 A1 | 8/2013 | Nishikawa et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0306226 A1 | 11/2013 | Zink |
| 2015/0173958 A1* | 6/2015 | Bunnelle .............. B32B 7/12 604/366 |
| 2017/0079848 A1 | 3/2017 | Piantoni |
| 2017/0165133 A1 | 6/2017 | Turner |
| 2019/0076301 A1* | 3/2019 | Schoon ........ A61F 13/15699 |

\* cited by examiner

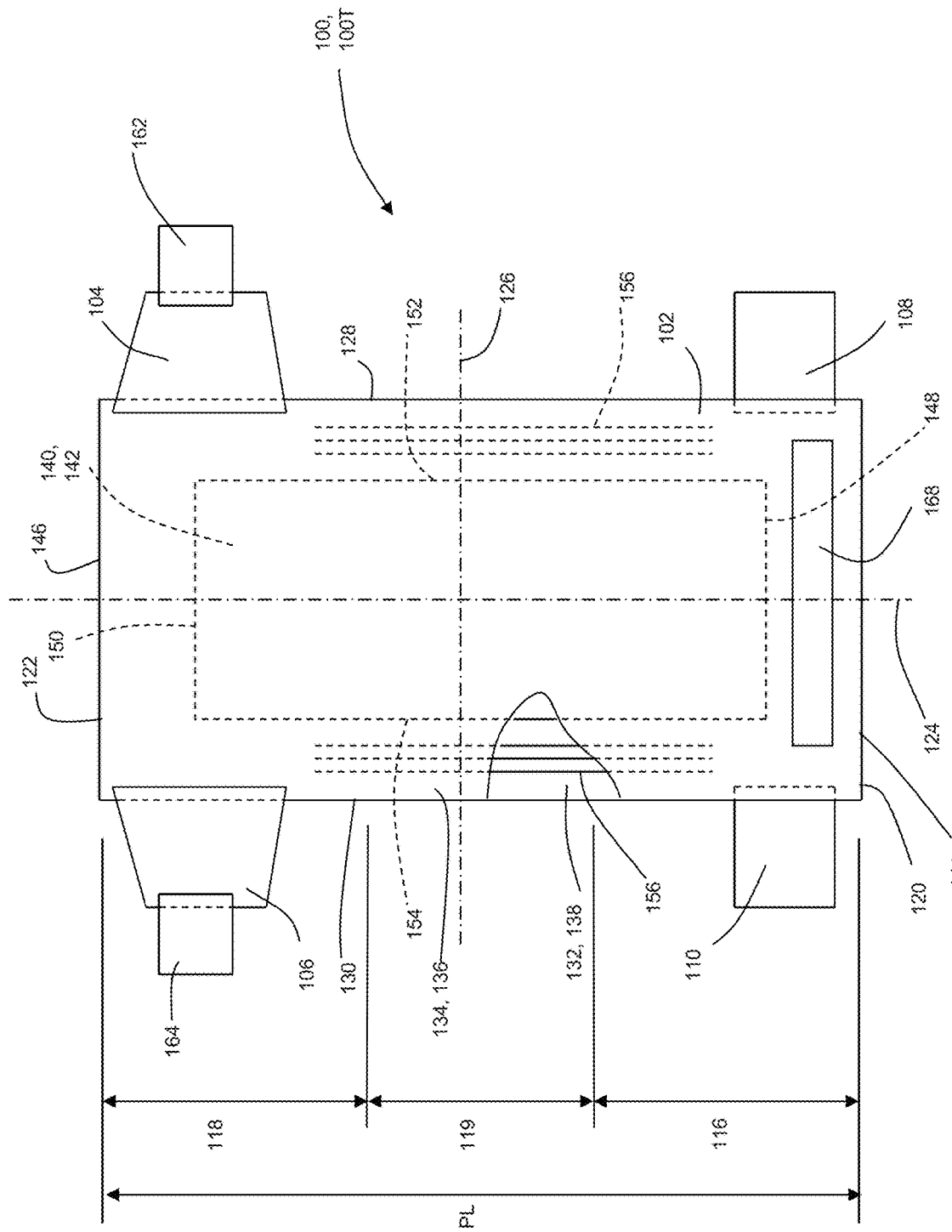

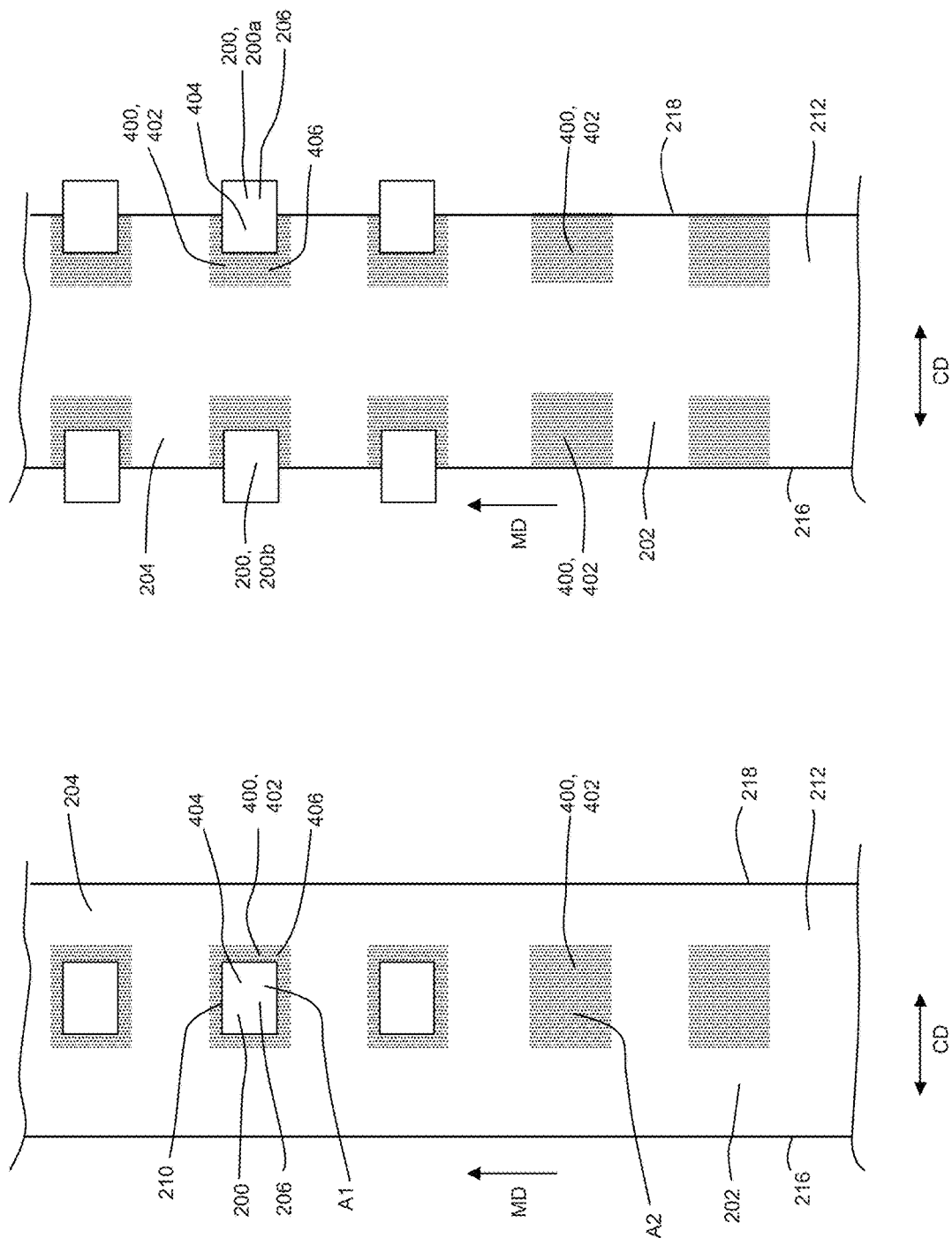

METHOD AND APPARATUS FOR BONDING SUBSTRATES

CROSS REFERENCE TO RELATED APPLICATIONS

This application claims the benefit of U.S. Provisional Application No. 62/718,071, filed on Aug. 13, 2018, the entirety of which is incorporated by reference herein.

FIELD OF THE INVENTION

The present disclosure relates to methods for manufacturing absorbent articles, and more particularly, to apparatuses and methods for bonding substrates that may be used as components of absorbent articles.

BACKGROUND OF THE INVENTION

Along an assembly line, various types of disposable absorbent articles, such as diapers, sanitary napkins, and pant liners, may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Webs of material and component parts used to manufacture sanitary napkins and/or panty liners may include: backsheets, topsheets, secondary topsheets, absorbent core components, release paper wrappers, and the like. Once the desired component parts are assembled, the advancing web(s) and component parts are subjected to a final knife cut to separate the web(s) into discrete absorbent articles. The absorbent articles may also sometimes be folded and/or individually wrapped.

When manufacturing absorbent articles, various components and/or advancing webs of material may be bonded together in various ways, such as with adhesives and/or mechanical bonding techniques. Some bonding operations may bond substrates together with hot melt adhesives that remain tacky even after the adhesives have cooled. However, utilizing such adhesives to bond discrete parts with other substrates can present various challenges in some types of assembly operations. For example, in some assembly operations, a first continuous substrate may be cut into discrete parts, such as waist bands for example. In turn, the discrete waistbands, may be bonded with a continuous substrate, such as a topsheet. With continued reference to a waistband and topsheet bonding operation as an example illustration, adhesive may be applied to either or both the discrete waistband and the topsheet. When applying adhesive to the discrete waistband prior to combining with the topsheet, applied adhesive may migrate from the waistband and contaminate material handling equipment, such as such as knives, drums, and conveyance devices utilized to place the waistband on the topsheet. Such contaminating adhesive may also migrate to other substrates and components of the assembled article. Instead of applying adhesive to the waistband, adhesive may be applied to the topsheet before combining with the waistband. As such, the adhesive may be applied to the topsheet in discrete patches that are sized to correlate or match with the size of the waistband. Such an operation requires very precise placement of the waistband on the discrete patches of adhesive. Misplacement of the waistbands on the adhesive may lead to portions of the waistbands being unbonded and may also lead to areas of exposed adhesive. In turn, exposed adhesive that remains tacky can act to unintentionally bond other components together. For example, in subsequent assembly operations, the combined waistband and topsheet may be combined with other advancing substrates and/or components to create discrete absorbent articles that are folded and packaged. As such, the absorbent article may become bonded to itself in the folded configuration.

In an attempt to avoid the above described negative affects resulting from exposed tacky adhesive in an assembled product, adhesives may be applied in areas that are smaller than the discrete part to be bonded. For example, adhesive may be applied to only central portions of discrete waistband before combining with a topsheet. In another scenario, adhesive may be applied to the topsheet in discrete patches that are relatively smaller than the size of the waistband. In turn, only the central region of a waistband may be bonded with the topsheet. As such, perimeter edges of the waistband may remain unbonded and loose. Such unbonded edges may be aesthetically unpleasing and may lead to undesired tearing and/or separation of the waistband during product use.

Consequently, it would be beneficial to provide a method and apparatus for bonding substrates to other substrates with adhesives applied thereto so as to bond entire areas of the substrates without the negative effects associated with exposed adhesives that remain tacky during subsequent assembly operations.

SUMMARY OF THE INVENTION

In one form, a method of bonding substrates comprises: providing a first substrate comprising a first surface and an opposing second surface; providing a second substrate comprising a first surface and an opposing second surface; applying a tackifier free adhesive to the first surface of the second substrate to define an adherence zone; positioning the first substrate on the adherence zone of the second substrate to define a first region of the adherence zone wherein the tackifier free adhesive is positioned between the second surface of the first substrate and the first surface of the second substrate, and a second region of the adherence zone wherein the tackifier free adhesive is not positioned between the second surface of the first substrate and the first surface of the second substrate; and pressing the first substrate and the second substrate against each other.

In another form, a method for making a laminate comprises: providing a discrete first substrate comprising a first surface and an opposing second surface, the discrete first substrate further comprising a first area; advancing a continuous second substrate comprising a first surface and an opposing second surface; heating a tackifier free adhesive; subsequent to heating, applying the tackifier free adhesive to the first surface of the continuous substrate to define an adherence zone comprising a second area, wherein the second area is greater than the first area; forming a laminate by positioning the discrete first substrate on the adherence zone on the continuous second substrate to define a first region of the adherence zone wherein the tackifier free adhesive is positioned between the second surface of the first substrate and the first surface of the second substrate, and a second region of the adherence zone wherein the tackifier free adhesive is not positioned between the second surface of the first substrate and the first surface of the second substrate; and pressing the discrete first substrate and the continuous second substrate against each other to force the tackifier free adhesive into the first substrate and the second substrate.

In yet another form, an absorbent article comprises: a laminate comprising: a first nonwoven comprising a first surface and an opposing second surface; a second nonwoven comprising a first surface and an opposing second surface; a tackifier free adhesive positioned on the first surface of the second nonwoven defining an adherence zone; wherein the first nonwoven is positioned on the adherence zone of the second nonwoven to define a first region of the adherence zone wherein the tackifier free adhesive bonds the first nonwoven with the second nonwoven and is positioned between the second surface of the first nonwoven and the first surface of the second nonwoven, and a second region of the adherence zone wherein the first nonwoven is not bonded with the second nonwoven; and wherein a portion of the tackifier free adhesive in the first region of the adherence zone is intermeshed with fibers between the first surface and the second surface of the second nonwoven and intermeshed with fibers between the first surface and the second surface of the first nonwoven.

BRIEF DESCRIPTION OF THE DRAWINGS

FIG. 1A is a partially cut away plan view of an absorbent article in the form of a taped diaper that may include one or more substrates bonded in accordance with the present disclosure with the portion of the diaper that faces away from a wearer oriented towards the viewer.

FIG. 5A is a side view of a first configuration of an advancing first substrate, second substrate, adherence zones, and laminate taken along the sectional line 5A-5A of FIG. 4.

FIG. 5B is a side view of a second configuration of advancing first substrates, second substrate, adherence zones, and laminate taken along the sectional line 5B-5B of FIG. 4.

DETAILED DESCRIPTION OF THE INVENTION

Figure 1B:
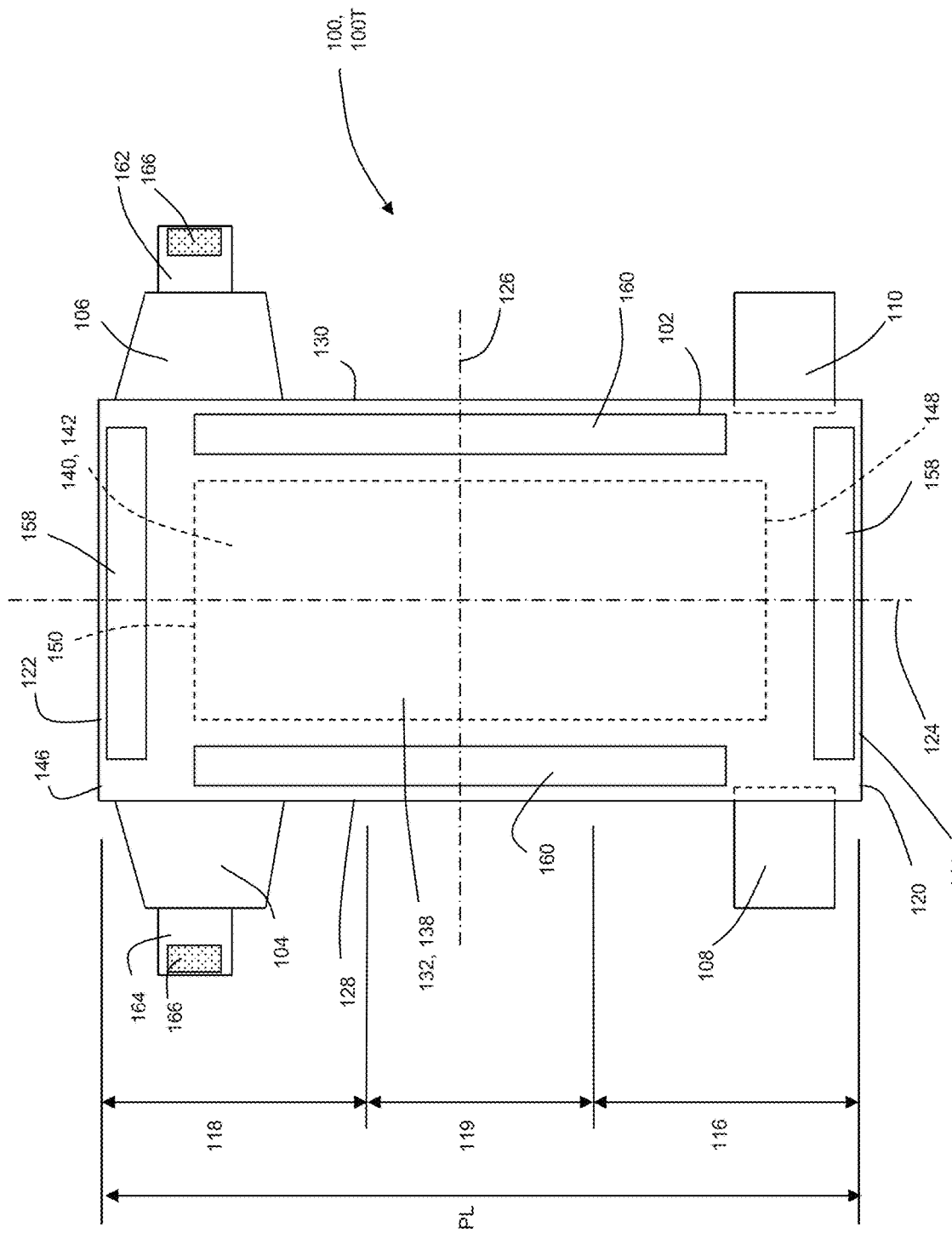
FIG. 1B is a plan view of the absorbent article of FIG. 1A that may include one or more substrates bonded in accordance with the present disclosure with the portion of the diaper that faces toward a wearer oriented towards the viewer.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The term "feminine hygiene articles" refers to disposable absorbent articles used by women for catamenial protection.

Such feminine hygiene articles may include sanitary napkins, tampons, interlabial products, incontinence devices, and pantiliners. Non-limiting examples of panty liners and sanitary napkins include those disclosed in U.S. Pat. Nos. 4,324,246; 4,463,045; 4,342,314; 4,556,146; 4,589,876; 4,687,478; 4,950,264; 5,009,653; 5,267,992; and 6,004,893.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the methods herein. For example, some nonwovens may have a basis weight of at least about 8 gsm, 12 gsm, 16 gsm, 20 gsm, 25 gsm, 25 gsm, 40 gsm, or 65 gsm. Some nonwovens may have basis weight of about 8 gsm to about 65 gsm, specifically reciting all 1 gsm increments within the above-recited ranges and all ranges formed therein or thereby.

It is to be appreciated that films having various basis weights can be used in accordance with the methods herein. For example, some films may have a basis weight of at least about 8 gsm, 12 gsm, 16 gsm, 20 gsm, 25 gsm, 25 gsm, 40 gsm, or 60 gsm. Some films may have basis weight of about 8 gsm to about 60 gsm, specifically reciting all 1 gsm increments within the above-recited ranges and all ranges formed therein or thereby.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "tackifier free adhesive" is used herein to refer to an adhesive composition comprising a polymer and/or a copolymer, wherein the adhesive composition if free of or devoid of tackifiers. Examples of such tackifier free adhesives are disclosed in U.S. Patent Application Nos. 62/660,338; 62/660,343; 62/660,353; 62/660,357; and 62/660,359, all of which are incorporated by reference herein.

"Devoid of" "free of" and the like, as those terms are used herein, means that the adhesive composition does not have more than trace amounts of background levels of a given material, ingredient, or characteristic following these qualifiers; the amount of the material or ingredient does not cause harm or irritation that consumers typically associate with the material or ingredient; or the material or ingredient was not added to the adhesive composition intentionally. In some applications, "devoid of" and "free of" can mean there is no measurable amount of the material or ingredient. For example, the adhesive composition in some forms can contain no measurable amount of a tackifier.

The term "tackifier" meats those conventional tackifier resins commonly available in the adhesive art and industry that are used in typical hot melt adhesives. Examples of conventional tackifier resins include aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, polyterpene, aromatic modified poly-terpene, terpene-phenolic, aromatic modified hydrogenated poly-cyclopentadiene resins, hydrogenated aliphatic resins, hydrogenated aliphatic aromatic resins, hydrogenated terpene and modified terpene, and hydrogenated rosin esters.

Aspects of the present disclosure relate to methods and apparatuses for bonding substrates used in absorbent articles, and in particular, methods and apparatuses for bonding a first substrate together a second substrate with hot melt adhesives that do not include tackifiers. Such tackifier free adhesives are relatively less tacky when cooled to a solid state. As discussed below, the first substrate comprises a first surface and an opposing second surface, and the second substrate comprises a first surface and an opposing second surface. The tackifier free adhesive may be applied to the first surface of the second substrate to define an adherence zone. The first substrate is positioned on the adherence zone of the second substrate to define a first region and a second region of the adherence zone to form a laminate. In the first region, the tackifier free adhesive is positioned between the second surface of the first substrate and the first surface of the second substrate. In the second region, the tackifier free adhesive is not positioned between the second surface of the first substrate and the first surface of the second substrate. In addition, the first substrate and the second substrate may be pressed against each other in the first region of the adherence zone to help the tackifier free adhesive to penetrate into the first substrate and the second substrate. When the first and second substrates are configured as nonwovens, penetration of the tackifier free adhesive into the nonwovens may help strengthen bond therebetween by enabling the tackifier free adhesive to intermesh with and bond with fibers within the nonwovens. The laminate may then be subjected to additional manufacturing and converting operations, such as combining, folding, and/or cutting operations, during assembly of an absorbent article. As the tackifier free adhesive cools in the adherence zone, the exposed tackifier free adhesive in the second region is less likely to unintentionally and undesirably cause the second substrate to become bonded to itself or other substrates and/or machinery during such subsequent assembly operations. Thus, the methods herein permit the application of the tackifier free adhesive to the second substrate to create an adherence zone defining a relatively large area that permits the placement of the first substrate thereon without the need to completely cover the adherence zone.

It is to be appreciated that the systems and methods disclosed herein are applicable to work with various types of converting processes and/or machines, such as for example, absorbent article manufacturing and assembly processes. The methods and apparatuses are discussed below in the context of manufacturing diapers. And for the purposes of a specific illustration, FIGS. 1A and 1B show an example of an absorbent article 100 that may be assembled in accordance with the methods and apparatuses disclosed herein. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes an absorbent chassis 102, first and second rear side panels 104 and 106; and first and second front side panels 108 and 110.

As shown in FIGS. 1A and 1B, the diaper 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the diaper 100 includes an inner, body facing surface 132, and an outer, garment facing surface 134. And the chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916, 661; 6,545,197; and 6,107,539.

As mentioned above, the diaper 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 100 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

The elasticized waistband 158 may provide improved fit and containment and may be a portion or zone of the diaper 100 that may elastically expand and contract to dynamically fit a wearer's waist. The elasticized waistband 158 may extend longitudinally inwardly from the waist edges 120, 122 of the diaper toward the lateral edges 148, 150 of the absorbent core 142. The diaper 100 may also include more than one elasticized waistband 158, for example, having one waistband 158 positioned in the back waist region 118 and one waistband 158 positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092. In some embodiments, the elasticized waistbands 158 may include materials that have been "pre-strained" or "mechanically prestrained" (subjected to some degree of localized pattern mechanical stretching to permanently elongate the material). The materials may be pre-strained using deep embossing techniques as are known in the art. In some embodiments, the materials may be pre-strained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107, 364; 4,209,563; 4,834,741; and 5,151,092.

As shown in FIG. 1B, the chassis 102 may include longitudinally extending and laterally opposing side flaps 160 that are disposed on the interior surface 132 of the chassis 102 that faces inwardly toward the wearer and contacts the wearer. Each side flap may have a proximal edge. The side flaps may also overlap the absorbent assembly 140, wherein the proximal edges extend laterally inward of the respective side edges of the absorbent assembly 152 and 154. In some configurations, the side flaps may not overlap the absorbent assembly. It is to be appreciated that the side flaps may be formed in various ways, such as for example, by folding portions of the chassis 102 laterally inward, i.e., toward the longitudinal axis 124, to form both the respective side flaps and the side edges 128 and 130 of the chassis 102. In another example, the side flaps may be formed by attaching an additional layer or layers to the chassis at or adjacent to each of the respective side edges and of the chassis. Each of the side flaps may be joined to the interior surface 132 of the chassis and/or the absorbent assembly in side flap attachment zones in the front waist region 116 and in side flap attachment zones in the back waist region 118. The side flaps may extend to the same longitudinal extent as the absorbent article or alternatively the side flaps may have a longitudinal extent that is less than the absorbent article.

Taped diapers may be manufactured and provided to consumers in a configuration wherein the front waist region and the back waist region are not fastened, pre-fastened, or connected to each other as packaged, prior to being applied to the wearer. For example, the taped diaper 100 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The diaper 100 may also include various configurations of fastening elements to enable fastening of the front waist region 116 and the back waist region 118 together to form a closed waist circumference and leg openings once the diaper is positioned on a wearer. For example, as shown in FIGS. 1A and 1B, the diaper 100 may include first and second fastening members 162, 164, also referred to as tabs, connected with the first and second rear side panels 104, 106, respectively. The diaper may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846, 815; 4,894,060; 4,946,527; 5,151,092; 5,221,274; 6,251, 097; 6,669,618; 6,432,098; and U.S. Patent Publication Nos. 2007/0078427 A1 and 2007/0093769 A1.

As previously mentioned, the fastening members 162 and 164 may be constructed from various materials and may be constructed as a laminate structure. The fastening members 162 and 164 may also be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the fastening members 162 and 164 may be pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the taped diaper. In some embodiments, the connection zone may be integrally formed as part of the backsheet 136 of the diaper 100 or may be formed as part of the first and second front panels 108, 110, such as described in U.S. Pat. Nos. 5,735,840 and 5,928,212.

Figure 2A:
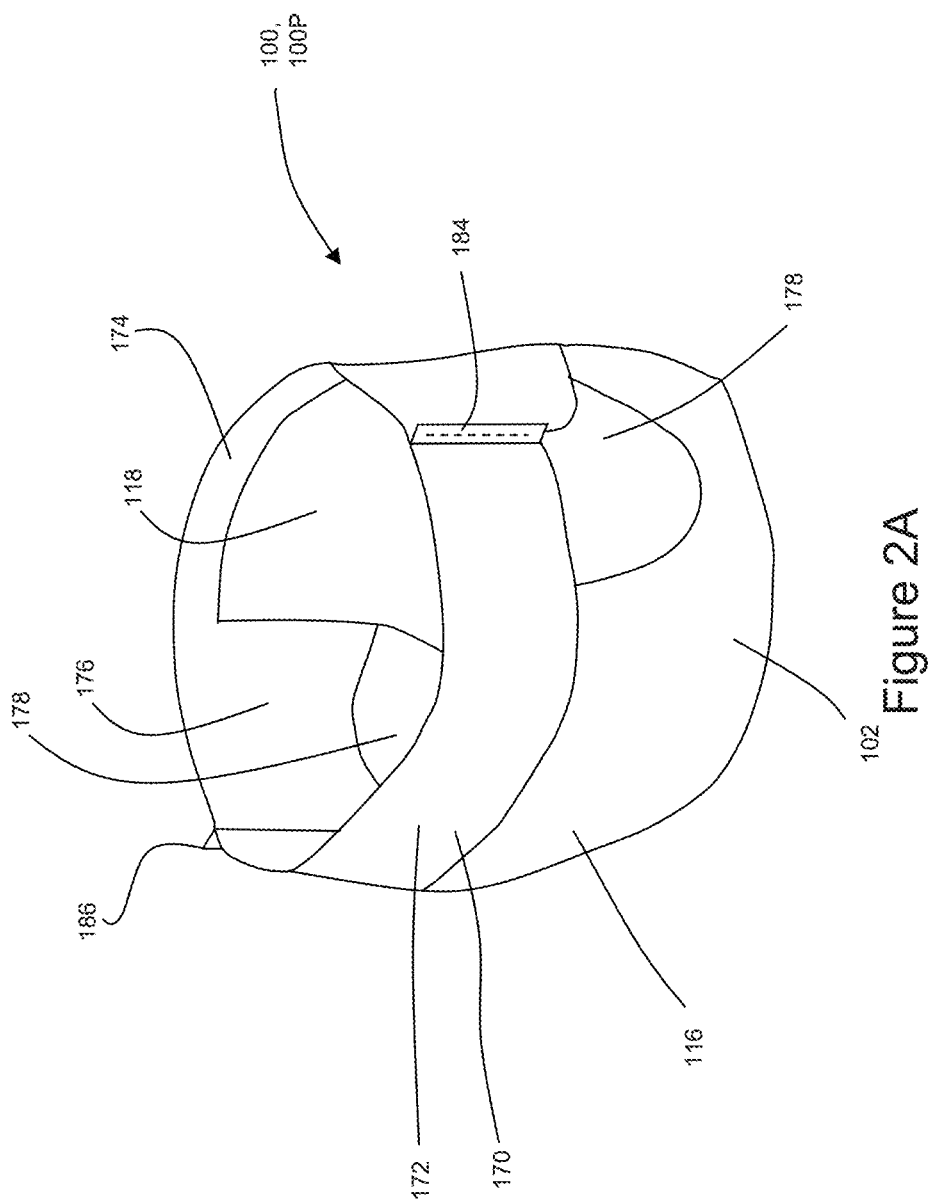
FIG. 2A is a front perspective view of an absorbent article that may include one or more substrates bonded in accordance with the present disclosure.
Figure 2C:
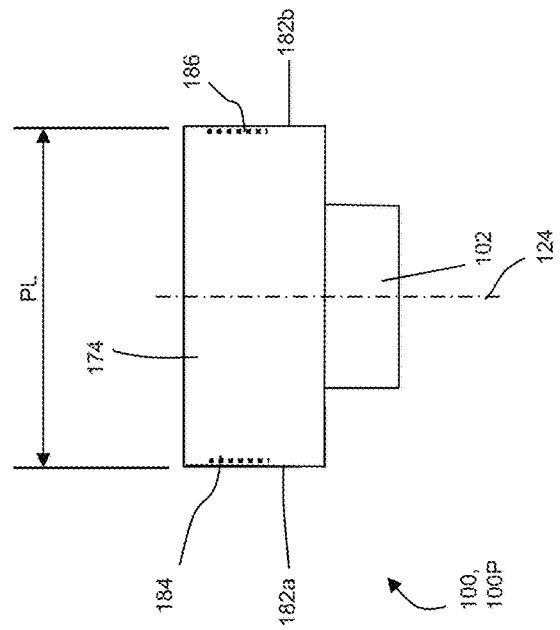
FIG. 2C is a rear view of the absorbent article of FIG. 2A.
Figure 2B:
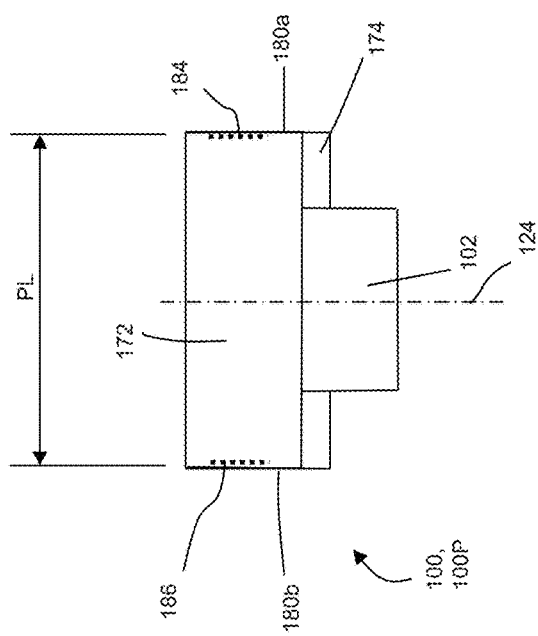
FIG. 2B is a front view of the absorbent article of FIG. 2A.

As previously mentioned, absorbent articles 100 may also be configured as diaper pants 100P having a continuous perimeter waist opening and continuous perimeter leg openings. For example, FIG. 2A shows a perspective view of an absorbent article 100 in the form of a diaper pant 100P in a pre-fastened configuration, and FIGS. 2B-2C show front and rear plan views of the diaper pant 100P. The diaper pant 100P may include a chassis 102 such a discussed above with reference to FIG. 1A and a ring-like elastic belt 170 such as shown in FIG. 2A. In some embodiments, a first elastic belt 172 and a second elastic belt 174 are bonded together to form the ring-like elastic belt 170. As such, diaper pants may be manufactured with the ring-like elastic belt 174 and provided to consumers in a configuration wherein the front waist region 116 and the back waist region 118 of the chassis 102 are connected to each other as packaged, prior to being applied to the wearer. As such, diaper pants may have a continuous perimeter waist opening 176 and continuous perimeter leg openings 178 such as shown in FIG. 2A.

As previously mentioned, the ring-like elastic belt 170 may be defined by a first elastic belt 172 connected with a second elastic belt 174. As shown in FIGS. 2A-2C, the first elastic belt 172 extends between a first longitudinal side edge 180a and a second longitudinal side edge 180b. And the second elastic 174 belt extends between a first longitudinal side edge 182a and a second longitudinal side edge 182b. The distance between the first longitudinal side edge 180a and the second longitudinal side edge 180b defines a pitch length, PL, of the first elastic belt 172, and the distance between the first longitudinal side edge 182a and the second longitudinal side edge 182b defines the pitch length, PL, of the second elastic belt 174. The first elastic belt is connected with the first waist region 116 of the chassis 102, and the second elastic belt 108 is connected with the second waist region 116 of the chassis 102. As shown in FIGS. 2A-2C, opposing end regions of the first elastic belt 172 are connected with opposing end regions of the second elastic belt 174 at a first side seam 184 and a second side seam 186 to define the ring-like elastic belt 170 as well as the waist opening 176 and leg openings 178. It is to be appreciated that the ring-like elastic belt may be formed by joining a first elastic belt to a second elastic belt with permanent side seams or with openable and reclosable fastening systems disposed at or adjacent the laterally opposing sides of the belts.

As previously mentioned, absorbent articles may be assembled with various components that may constructed with the laminates described herein. Thus, in the context of the previous discussion, the apparatuses and methods herein may be used to bond substrates configured as continuous substrates and/or discrete components of an absorbent article 100. For example, the apparatuses and methods herein may be utilized to bond substrates to create laminates to be used as or with any of the topsheet 138; backsheet 136; absorbent core 140; leg cuffs 156; waist feature 158; side panels 104, 106, 108, 110; connection zones 168; fastening elements 162, 164, 166, and/or belts before, during, and/or after the manufacture of an absorbent article 100.

Figure 3:
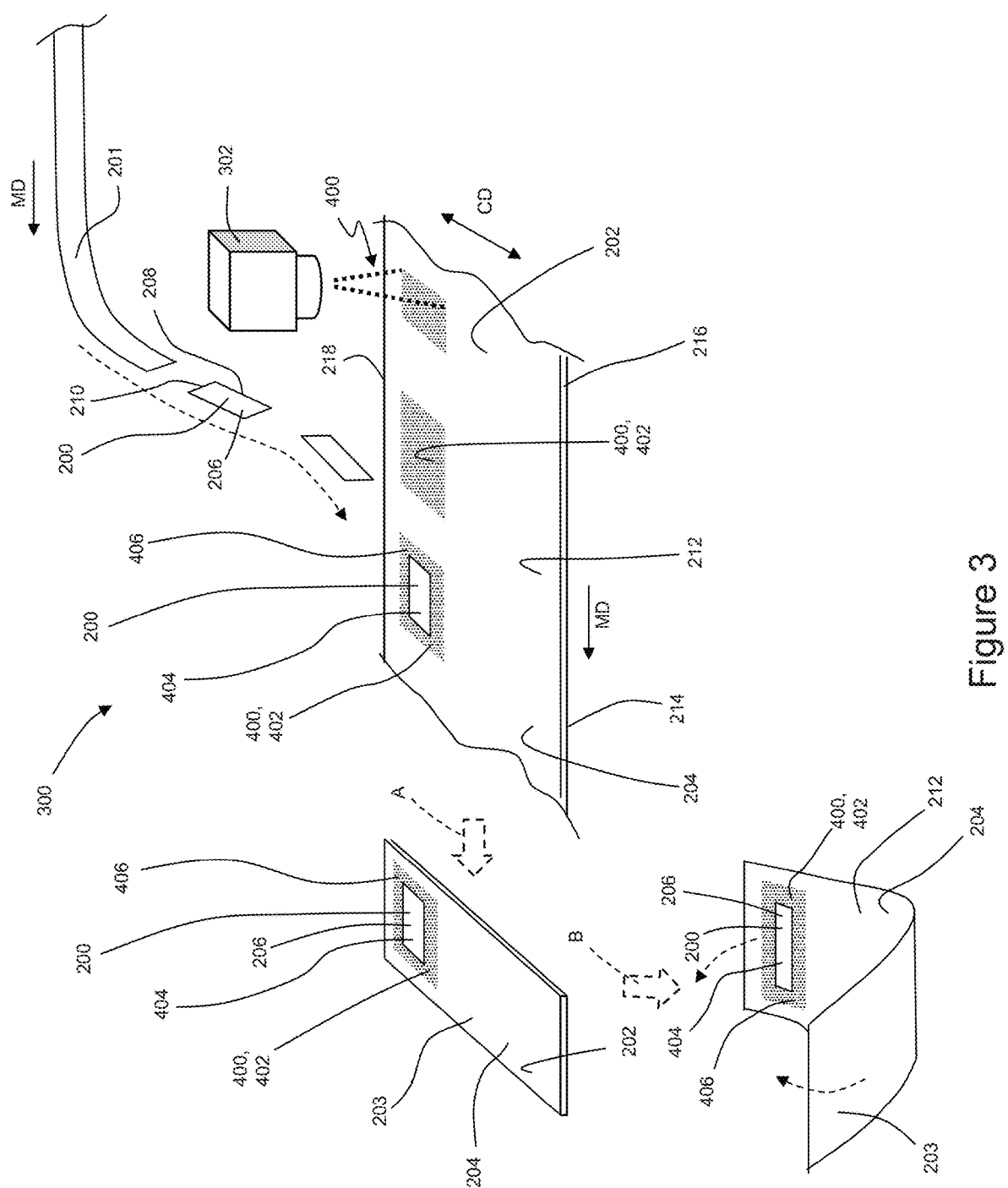
FIG. 3 is a schematic side view of an apparatus for assembling a laminate with a tackifier free adhesive.

It is to be appreciated that the systems and methods disclosed herein are applicable to work with various types of converting processes and/or machines. For example, FIG. 3 shows a schematic representation of a converting process including a bonding apparatus or system 300 that bonds a first substrate 200 with a second substrate 202 to form a laminate 204. The first substrate 200 includes a first surface 206 and an opposing second surface 208. In some configurations, the first substrate 200 may also be configured as a discrete piece or part that may be cut or otherwise separated from a continuous first substrate 201. As such, the shape of the first substrate 200 may be defined by a continuous perimeter edge 210. The second substrate 202 includes a first surface 212 and an opposing second surface 214. In some configurations, the second substrate 202 may be configured as a continuous second substrate advancing in a machine direction MD. The second substrate 202 may also define a width extending in the cross direction CD between a first longitudinal side edge 216 and a second longitudinal side edge 218.

As shown in FIG. 3, the bonding system 300 may include an adhesive applicator 302. During operation, the second substrate 204 advances in the machine direction MD. In turn, the adhesive applicator 302 deposits tackifier free adhesive 400 onto the first surface 212 of the advancing second substrate 202 to define an adherence zone 402. The first substrate 200 is positioned on the adherence zone 402 on the second substrate 202 to define a first region 404 and a second region 406 of the adherence zone 402. In the first region 404 of the adherence zone 402, the tackifier free adhesive 400 is positioned between the second surface 208 of the first substrate 200 and the first surface 212 of the second substrate 202. And in the second region 406 of the adherence zone 402, the tackifier free adhesive 400 is not positioned between the second surface 208 of the first substrate 200 and the first surface 212 of the second substrate 202.

With continued reference to FIG. 3, the tackifier free adhesive 400 in the second region 406 may remain exposed or otherwise uncovered by the first substrate 200 as the laminate 204 advances to additional downstream, subsequent manufacturing and converting operations, such as combining, folding, and/or cutting operations. Such additional subsequent operations are represented by the dashed arrow "A" that generically represents converting the laminate 204 into at least one discrete article 203. As such, the article 203 may include exposed tackifier free adhesive 400 in the second region 406 of the adherence zone 402 wherein second substrate 202 does not unintentionally become bonded to itself or other substrates and/or machinery during such additional subsequent operations. For example, FIG. 3 shows an additional subsequent operation of folding (represented by the dashed arrow "B") the discrete article 203 and the second substrate 202. As a result of folding, a portion of the first surface 212 of the second substrate 202 may be positioned into direct contact with the first surface 206 of the first substrate 200 and the second region 406 of the adherence zone 402. In turn, the tackifier free adhesive 400 does not bond the second substrate 202 and unintentionally hold the article 203 in a folded state. It is to be appreciated that the discrete article 203 may be in various forms and types, such as, for example, absorbent articles including feminine hygiene articles, diapers, sanitary napkins, and panty liners. It is also to be appreciated that the tackifier free adhesive 400 in the second region may be exposed to a wearer's skin and/or clothing during use of the article without unintentionally bonding to the wearer's skin and/or clothing.

Figure 4:
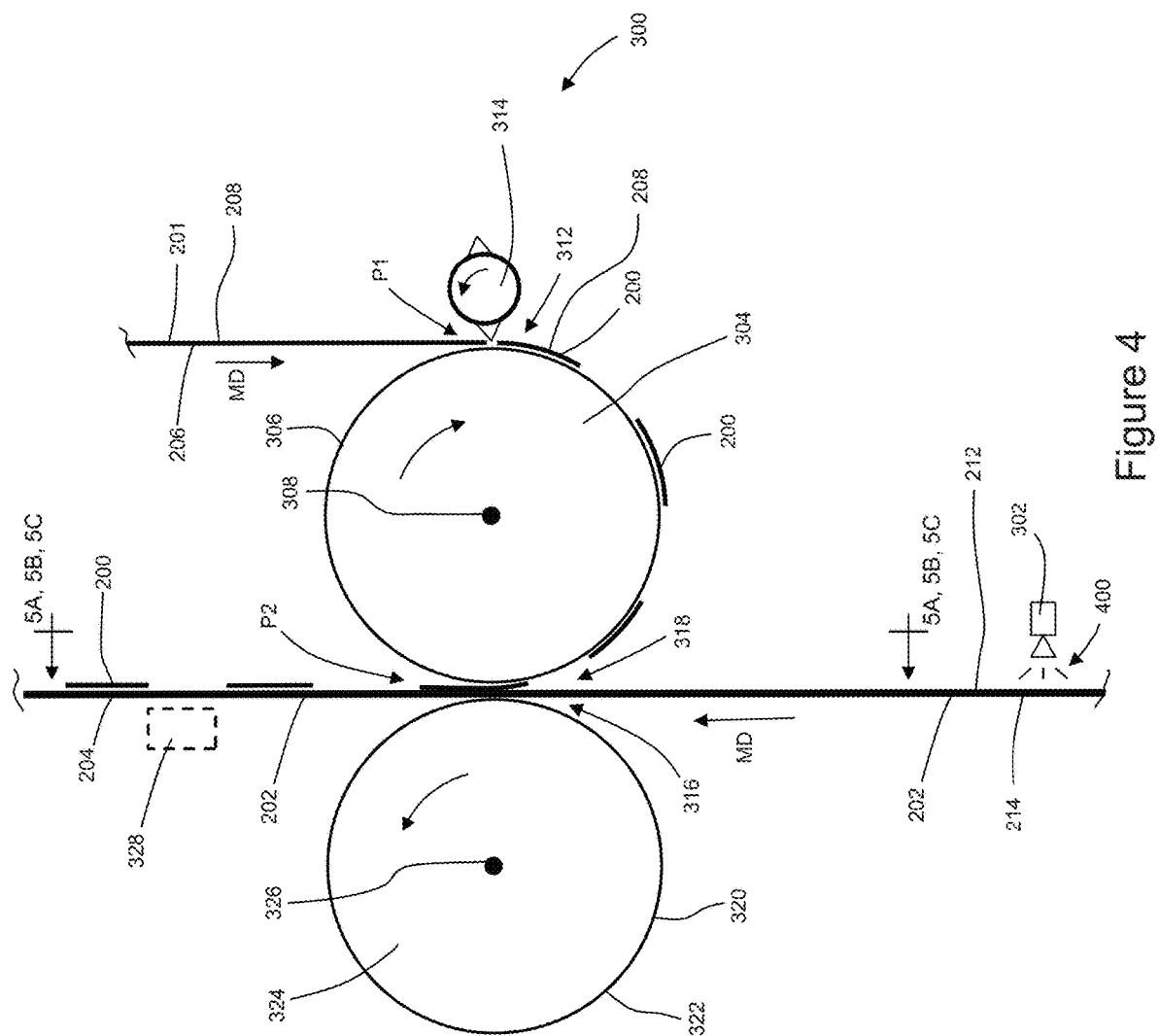
FIG. 4 is a left side view of an apparatus for assembling a laminate with a tackifier free adhesive.

It is to be appreciated that various process configurations may utilized to bond a first substrate 200 and a second substrate 202 with tackifier free adhesives to form the laminates 204 described herein. For example, FIG. 4 shows a schematic view of an example configuration of an apparatus 300 that may be utilized to form a laminate 204. The apparatus 300 may include a transfer assembly 304 configured to transport first substrates 200 in the form of discrete parts in a machine direction MD from a first position P1 to a second position P2. As shown in FIG. 4, a continuous first substrate 201 advances in a machine direction MD to the transfer assembly 304. The transfer assembly 304 may include a carrier surface 306 and may be adapted to rotate about a first axis 308. The first surface 206 of the advancing continuous first substrate 201 engages the moving carrier surface 306 at a pick-up zone 312. As the transfer assembly 304 is rotated about the first axis 308 to advance a portion of the continuous first substrate 201, a cutter 314 cuts a discrete first substrate 200 from the continuous first substrate 201 at the pick-up zone 312. It is to be appreciated that the cutter 314 may be configured in various ways, such as for example, a knife or a laser.

Although the transfer assembly 304 is depicted as rotating drum, it is to be appreciated that the transfer assembly may be configured in various ways. For example, in some embodiments, the transfer assembly 304 may be in the form of a conveyor belt and/or one or more drums and/or other types of conveyance apparatuses, such as disclosed for example in U.S. Pat. Nos. 5,025,910; 5,224,405; 5,556,504; 5,702,551; 6,319,347; 6,450,321; 6,524,423; 6,550,517; 6,604,623; 6,116,317; 6,649,010; 6,722,494; 7,341,087; 7,650,984; 7,770,712; 8,720,666; and 9,737,442 and U.S. Patent Publication No. 2009/0294044 A1, all of which are incorporated by reference herein. In some configurations, the transfer assembly 304 may rotate about the first axis 308 at a constant or variable angular velocity. In some configurations, the carrier surface 306 may orbit the first axis 308 at a constant or variable angular velocity and/or at a constant or variable speed. It is also to be appreciated that the carrier surface 306 may advance at a speed that is equal to or greater than the advancement speed of the continuous first substrate 201. In some configurations wherein the continuous first substrate 201 has been stretched in the machine direction before engaging the transfer assembly 304, the carrier surface 306 may advance at a speed that is less than the advancement speed of the continuous first substrate 201. In some configurations, the carrier surface 306 may orbit the first axis 308 at a constant or variable distance from the first axis 308. It is also to be appreciated that the carrier surface 306 herein may be arranged with various quantities of apertures having various shapes and sizes, and may be in fluid communication with a vacuum system. In addition, while orbiting from the first position P1 to the second position P2, the carrier surface 306 and the first substrate 200 may also be rotated or pivoted about a second axis of rotation to place the first substrate 200 in a second orientation.

With continued reference to FIG. 4, the transfer assembly 304 is rotated about the first axis 308 such that the carrier surface 306 and the first substrate 200 positioned on the carrier surface 306 orbit about the first axis 308 from the first position P1 to the second position P2. The first substrate 200 is then transferred to the second substrate 202 at a drop-off zone 316 to form the laminate 204. With particular reference to FIGS. 4 and 5A, the second substrate 202 advances in the machine direction MD past the adhesive applicator 302 and toward the drop-off zone 316. The adhesive applicator 302 deposits tackifier free adhesive 400 on the first surface 212 of the second substrate 202 to define an adherence zone 402 of the second substrate 202. At the drop-off zone 316, the first substrate 200 is transferred from the transfer assembly 304 to position the second surface 208 of the first substrate 200 on the adherence zone 402. It is to be appreciated that the carrier surface 306 may advance at various speeds through the drop-off zone 316 relative to the advancement speed of the second substrate 202. In some configurations, the carrier surface 306 may advance at the same speed as the advancement speed of the second substrate 202 through the drop off zone 316. In some configurations, the carrier surface 306 may advance at a speed that is slower than the advancement speed of the second substrate 202 through the drop off zone 316.

As shown in FIGS. 4 and 5A, the adherence zone 402 of the laminate 204 may include a first region 404 and a second region 406. The tackifier free adhesive 400 is positioned between the second surface 208 of the first substrate 200 and the first surface 212 of the second substrate 202 in the first region 404 of the adherence zone 402. And the tackifier free adhesive 400 is not positioned between the second surface 208 of the first substrate 200 and the first surface 212 of the second substrate 202 in the second region 406 of the adherence zone 402.

It is to be appreciated that the adherence zone 402 and the first substrate 200 may have various shapes. For example, although the adherence zone 402 is generically depicted herein as defining a rectangular shape on the first surface 212 of the second substrate 202, it is to be appreciated that the adherence zone 402 may have a perimeter that defines circular, square, oval, elliptical, and various types of other shapes that may or may not correspond with shapes defined by all or portions of the perimeter 210 of the first substrate 200. It is to be appreciated that the adherence zone 402 and the first substrate 200 may have the same shape or may have different shapes.

It is to be appreciated that the adherence zone 402 and the first substrate 200 may have various sizes relative to each other. For example, as shown in FIG. 5A, the first substrate may define a first area A1 and the adherence zone 402 may define a second area A2. In some configurations, the second area A2 may be greater than the first area A1. In some configurations, the first area A1 may be equal to the second area A2. It is also to be appreciated that the first substrate 200 may be oriented relative to the second substrate 202 and/or the adherence zone 402 in various ways. For example, as shown in FIG. 5B, the first substrate 200 may be oriented on the second substrate 202 such that a portion of the second surface 208 of the first substrate 200 may not be entirely positioned on the first surface 212 of the second substrate 202 and/or the adherence zone 402.

Figure 5C:
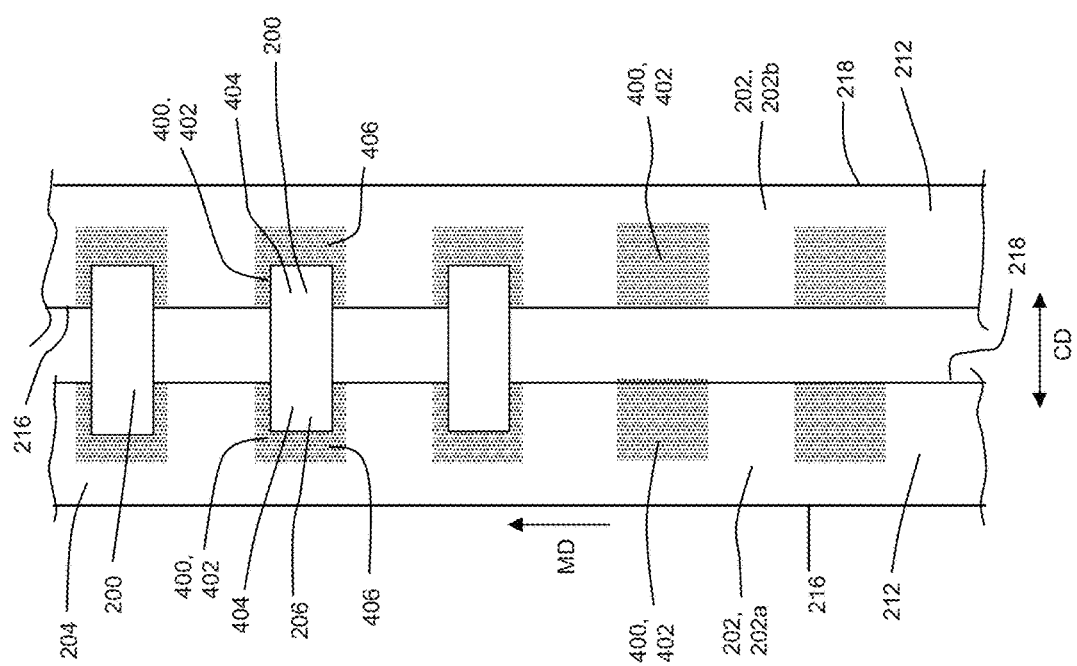
FIG. 5C is a side view of a third configuration of advancing first substrates, second substrates, adherence zones, and laminate taken along the sectional line 5C-5C of FIG. 4.

It is also to be appreciated that the apparatus 300 may be configured to assemble laminates 204 with a plurality of first substrates 200 and/or second substrates 202 in various orientations. For example, such as shown in FIG. 5B, the laminate 204 may include a plurality of first substrates 200a, 200b arranged in along the machine direction MD on the first edge 216 and second edge 218, respectively, of the second substrate 202 and corresponding adherence zones 402. In another example, such as shown in FIG. 5C, the laminate 204 may include second substrates 202a, 202b separated from each other in cross direction CD with first substrates 200 arranged in along the machine direction MD and partially posited on both the second substrates 202a, 202b and corresponding adherence zones 402. It is also to be appreciated that the adhesive applicator 302 can be configured to apply tackifier free adhesive 400 so as to define a plurality of adherence zones 402 arranged along the machine direction MD and/or cross direction on the second substrate 202, such as shown for example in FIGS. 5A-5C. In some configurations, the adhesive applicator 302 may be configured to apply tackifier free adhesive 400 either or both the first substrate 200 and the second substrate 202.

The apparatuses 300 herein may also be configured in various ways to help enhance the bonding between the first and second substrates 200, 202 in the adherence zone 402. In some configurations, such as shown in FIG. 4, the first substrate 200 and/or the second substrate 202 may include nonwoven layers that are combined to form the laminate 204. In turn, the laminate 204 may advance through a nip 318 that is adapted to press first substrate 200 together with the second substrate 202 in the first region 404 of the adherence zone 402 to help the tackifier free adhesive 400 to penetrate into the first and second substrates 200, 202. When the first and second substrates 200, 202 include nonwoven layers, penetration of the tackifier free adhesive into the nonwovens may cause the tackifier free adhesive to intermesh with and bond with fibers within the nonwovens to help strengthen bonds therebetween. For example, with configuration shown in FIG. 4, the nip 318 may defined between a pressing surface 320 and the carrier surface 306. As the first substrate 200 is transferred from the transfer assembly 304 to the second substrate 202, the pressure is exerted on the second surface 214 of the second substrate 202 by pressing surface 320 and on the first surface 206 of the first substrate 200 by the carrier surface 306. In turn, the pressure exerted on the first and second substrates 200, 202 may force the tackifier free adhesive 400 in the adherence zone 402 through the first surface 212 of the second substrate 202 and through the second surface 208 of the first substrate 200. As such, a portion of the tackifier free adhesive 400 in the first region 404 of the adherence zone 402 may become intermeshed with fibers between the first surface 212 and the second surface 214 of the second substrate 202 and intermeshed with fibers between the first surface 206 and the second surface 208 of the first substrate 200.

As shown in FIG. 4, the pressing surface 320 may be defined by an outer circumferential surface 322 of a drum 324, wherein the drum 324 may be adapted to rotate about a second axis of rotation 326. It is to be appreciated that the pressing surface 320 may be configured in various ways. For example, the pressing surface 320 may be associated with various types of apparatuses, such as for example, a rotating bump roll, an oscillating tamper, and/or various types of configurations such as disclosed in U.S. Pat. Nos. 4,576,600; 6,494,244; 7,452,436; 7,640,962; 7,811,403; and 9,168,182; and U.S. Patent Publication No. U.S. Patent Publication No. 2009/0294044 A1, all of which are incorporated by reference herein. Although FIG. 4 depicts the nip 318 as being located and defined between the carrier surface 306 of the transfer assembly 304 and the pressing surface 320 of the drum 324, it is to be appreciated that the apparatus 300 may be configured with one or more nips 320 positioned downstream of the drop off zone 316 adapted to press the first and second substrates 200, 202 against each other in the adherence zone 402. Such nips may be configured in various ways and may be defined between various types of apparatuses, such as discussed herein.

With reference to FIGS. 3 and 4, it is to be appreciated that the adhesive applicator 302 may be configured to apply the tackifier free adhesive 400 in various ways. For example, the adhesive applicator may be configured as a slot coating applicator or a meltblowing applicator. In some configurations, the tackifier free adhesive 400 may be heated before reaching the adhesive applicator 302 and/or may be heated while flowing through the adhesive applicator 302.

The apparatuses 300 herein may include one or more cooling apparatuses 328, generically represented in FIG. 4 by a dashed rectangle, adapted remove heat energy from the first region 404 and/or the second region 406 of the adherence zone 402. It is to be appreciated that such cooling apparatuses 328 may be configured in various ways. In some configurations, the cooling apparatus 328 may include a heat exchanger, such as a heat sink. For example, the apparatus 300 may be configured to advance the laminate 204 to a cooling apparatus 328 configured as one or more chill rolls, wherein the laminate 204 may partially wrap around a cooling surface of a chill roll. In some configurations, the cooling apparatus 328 may include a device, such as a fan or blower, moves air or other gas along the second surface 202 of the second substrate 202 and/or the first surface 206 of the first substrate 200 and the first surface 212 of the second substrate 202 to remove heat energy from the adherence zone 402 with convection. Although the cooling apparatus 328 schematically represented in FIG. 4 is adjacent the second surface 214 of the second substrate 202, it is to be appreciated that the cooling apparatus 328 may be configured with components that are in close proximity with or in contact with the first surface 212 and/or second surface 214 of the second substrate 202 and/or the first surface 206 of the first substrate 200.

Figure 6:
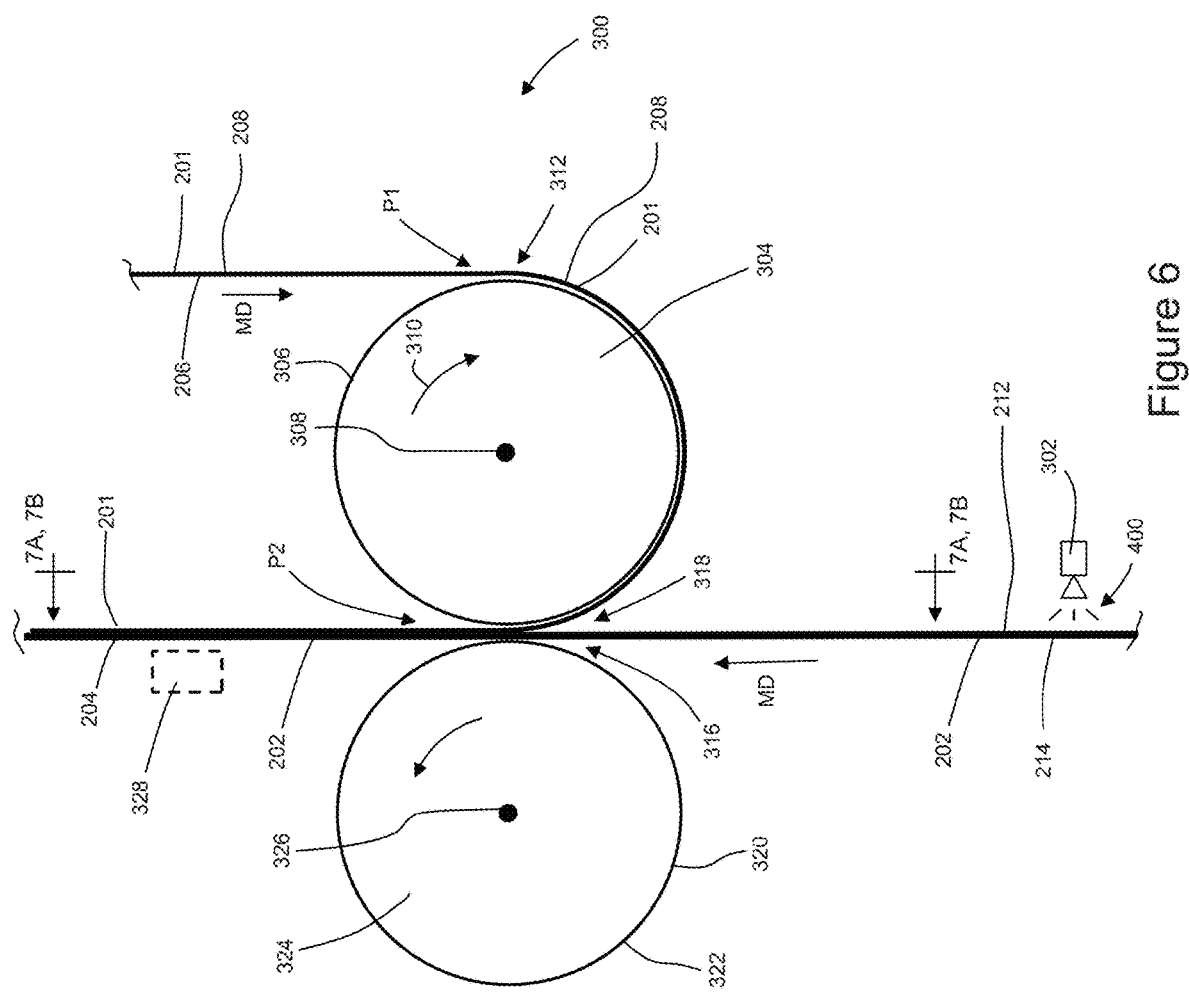
FIG. 6 is a left side view of an apparatus for assembling a laminate with a tackifier free adhesive.

As previously mentioned, the apparatuses and methods herein may also be used to bond substrates configured as continuous substrates. For example, FIG. 6 shows a schematic view of an example configuration of an apparatus 300 that may utilize a tackifier free adhesive 400 to bond a continuous first substrate 201 with a continuous second substrate 202 to form a laminate 204. The apparatus 300 may include a transfer assembly 304, such as described above, to transport the first substrate 201 in a machine direction MD from a first position P1 to a second position P2. As shown in FIG. 6, a continuous first substrate 201 advances in a machine direction MD to the transfer assembly 304. The first surface 206 of the advancing continuous first substrate 201 engages the moving carrier surface 306 at a pick-up zone 312. With continued reference to FIG. 6, the transfer assembly 304 is rotated about the first axis 308 such that the carrier surface 306 and the continuous first substrate 201 positioned on the carrier surface 306 orbit about the first axis 308 from the first position P1 to the second position P2. The continuous first substrate 201 is then transferred to the continuous second substrate 202 at a drop-off zone 316 to form the laminate 204.

Figure 7B:
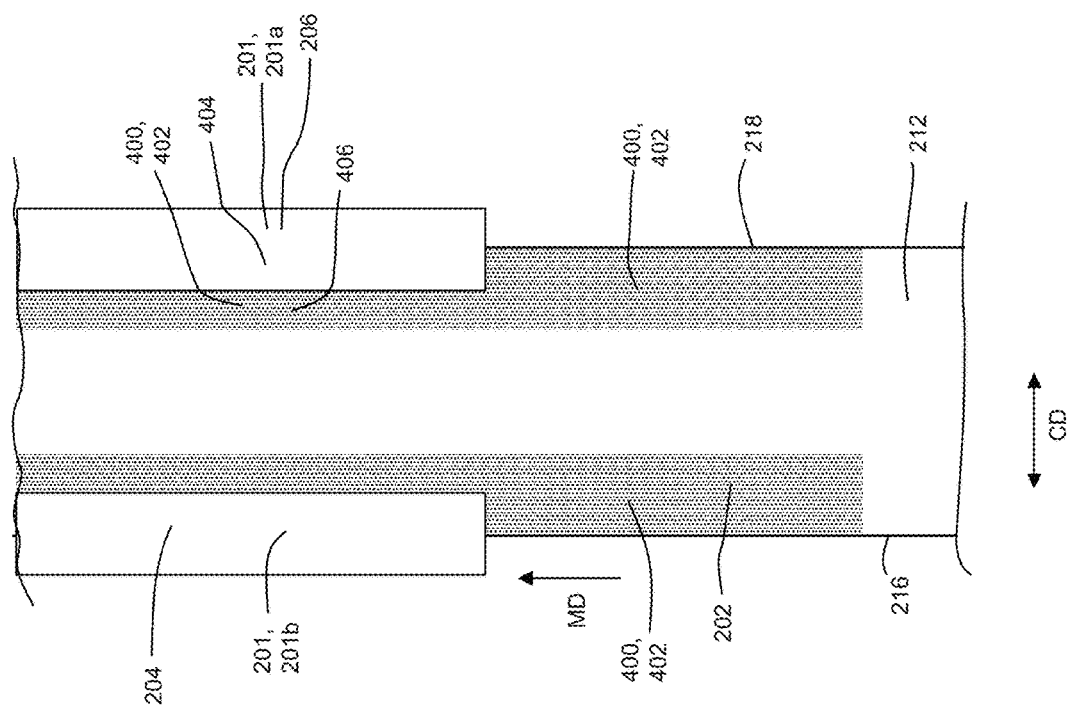
FIG. 7B is a side view of a second configuration of advancing first substrates, second substrate, adherence zones, and laminate taken along the sectional line 7B-7B of FIG. 6.
Figure 7A:
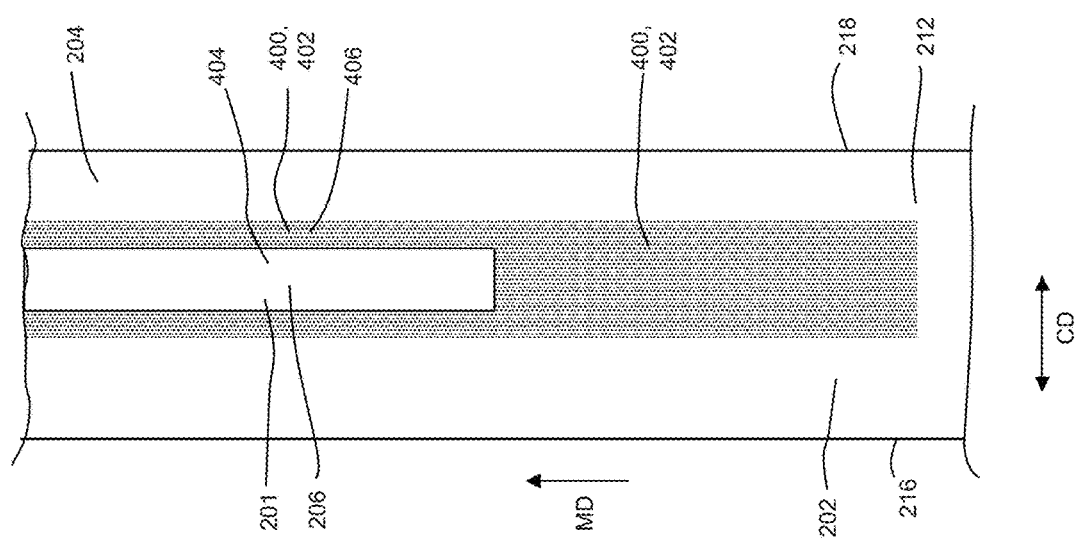
FIG. 7A is a side view of a first configuration of an advancing first substrate, second substrate, adherence zones, and laminate taken along the sectional line 7A-7A of FIG. 6.

With particular reference to FIGS. 6 and 7A, the continuous second substrate 202 advances in the machine direction MD past the adhesive applicator 302 and toward the drop-off zone 316. The adhesive applicator 302 deposits tackifier free adhesive 400 on the first surface 212 of the second substrate 202 to define an adherence zone 402 of the second substrate 202. At the drop-off zone 316, the continuous first substrate 201 is transferred from the transfer assembly 304 to position the second surface 208 of the continuous first substrate 201 on the adherence zone 402.

As shown in FIGS. 6 and 7A, the adherence zone 402 of the laminate 204 may include a first region 404 and a second region 406. The tackifier free adhesive 400 is positioned between the second surface 208 of the continuous first substrate 201 and the first surface 212 of the continuous second substrate 202 in the first region 404 of the adherence zone 402. And the tackifier free adhesive 400 is not positioned between the second surface 208 of the continuous first substrate 201 and the first surface 212 of the continuous second substrate 202 in the second region 406 of the adherence zone 402. As discussed above, it is to be appreciated that the adherence zone 402 and the continuous first substrate 201 may have various shapes. For example, although the adherence zone 402 is generically depicted herein as defining a continuous rectangular shape on the first surface 212 of the second substrate 202, it is to be appreciated that the adherence zone 402 may have edges that defines circular, square, oval, elliptical, and various types of other shapes that may or may not correspond with shapes defined by all or portions of edges of the continuous first substrate 201. It is to be appreciated that the adherence zone 402 and the continuous first substrate 201 may have edges having the same shapes or may have different shapes.

It is also to be appreciated that the continuous first substrate 201 may be oriented relative to the second substrate 202 and/or the adherence zone 402 in various ways. For example, as shown in FIG. 7B, the continuous first substrate 201 may be oriented on the second substrate 202 such that a portion of the second surface 208 of the first substrate 201 may not be entirely positioned on the first surface 212 of the second substrate 202 and/or the adherence zone 402. In addition, it is also to be appreciated that the apparatus 300 may be configured to assemble laminates 204 with a plurality of continuous first substrates 201 and/or continuous second substrates 202 in various orientations. For example, such as shown in FIG. 7B, the laminate 204 may include continuous first substrates 201a, 201b arranged in along the machine direction MD on the first edge 216 and second edge 218, respectively, of the second substrate 202 and corresponding adherence zones 402. As previously mentioned, the adhesive applicator 302 may be configured to apply tackifier free adhesive 400 either or both the continuous first substrate 201 and the continuous second substrate 202.

As described above, the laminates 204 discussed herein may be used as to construct various different components used in the manufacture of different types of absorbent articles. For example with reference to FIGS. 1A, 1B, and 2A-2C, the laminates 204 herein may be used to form all or portions of components such as: chassis 102; side panels 104, 106, 108, 110; belts 172, 174; backsheets 136; topsheets 138; absorbent assembly 140; leg cuffs 156; waistband 158; side flaps 160; fastening members 162, 164; and/or connection zone 168. For example, with reference to FIG. 5A, transfer assemblies 304 with carrier surfaces 306 as disclosed herein may be utilized to apply first substrates 200 in the form of waistbands 158 to a second substrate 202 in the form an advancing topsheet substrate 138. In another example, with reference to FIG. 5B, transfer assemblies 304 with carrier surfaces 306 as disclosed herein may be utilized to apply first substrates 200a, 200b in the form of side panels 104, 106, 108, 110 to a second substrate 202 in the form an advancing topsheet substrate 138 and/or advancing backsheet substrate 136. In yet another example, with reference to FIG. 5C, transfer assemblies 304 with carrier surfaces 306 as disclosed herein may be utilized to apply first substrates 200 in the form of chassis 102 to second substrates 202a, 202b in the form an advancing first belt 172 and second belt 174. In still another example, with reference to FIG. 7A, transfer assemblies 304 with carrier surfaces 306 as disclosed herein may be utilized to apply continuous first substrates 201 in the form of a topsheet substrate 138 to a second substrate 202 in the form an advancing backsheet substrate 136. In yet another example, with reference to FIG. 7B, transfer assemblies 304 with carrier surfaces 306 as disclosed herein may be utilized to apply continuous first substrates 201 in the form of leg cuffs 156 to a second substrate 202 in the form an advancing topsheet substrate 138.

In another example, the processes herein may be utilized in assembling laminates 204 to form side seams 184, 186 on diaper pants 100P, such as described above with reference to FIGS. 2A-2C. For example, as described below with reference to FIGS. 8-10, tackifier free adhesive 400 may be used to connect opposing end regions of the first elastic belt 172 with opposing end regions of the second elastic belt 174 at a first side seam 184 and a second side seam 186 to define the ring-like elastic belt 170 as well as the waist opening 176 and leg openings 178.

Figure 8:
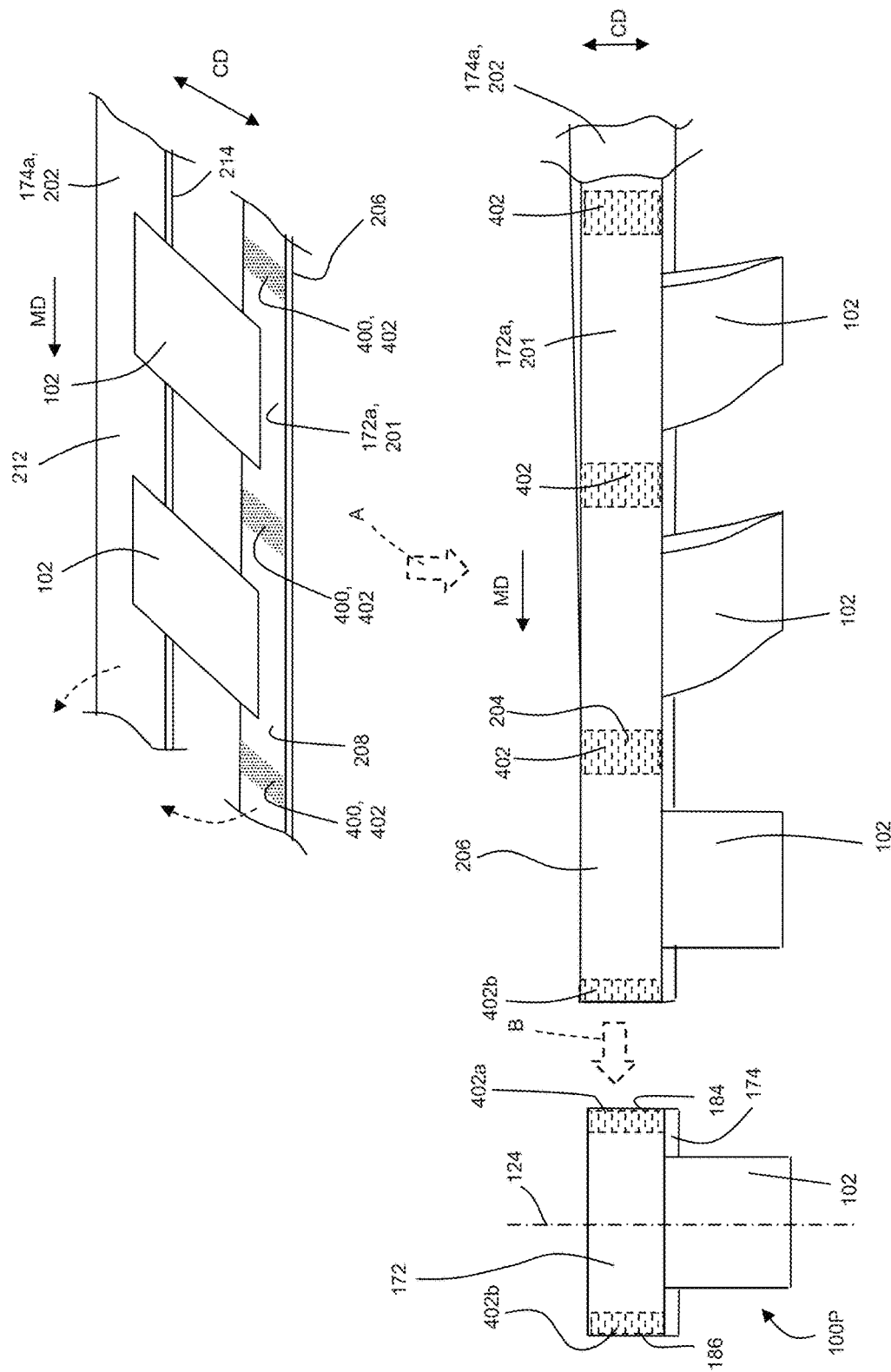
FIG. 8 is a schematic illustration of a diaper pant assembly process with elastomeric laminates.

As shown in FIG. 8, when assembling diaper pants 100P, the first substrate 201 may be in the form of a first elastic belt laminate 172*a*, and the second substrate 202 may be in the form of a second elastic belt laminate 174*a*. The first elastic belt laminate 172*a* and the second elastic belt laminate 174*a* may be separated from each other in the cross direction CD and may be connected with each other with a plurality of chassis 102 intermittently spaced along the machine direction MD. As also illustrated in FIG. 8, tackifier free adhesive 400 may be applied to the second surface 208 of the first substrate 202 to define adherence zones 402. The adherence zones 402 may be in the form of discrete zones positioned between adjacent chassis 102. In some configurations, the adherence zones 402 may extend continuously along the machine direction MD.

Figure 8A:
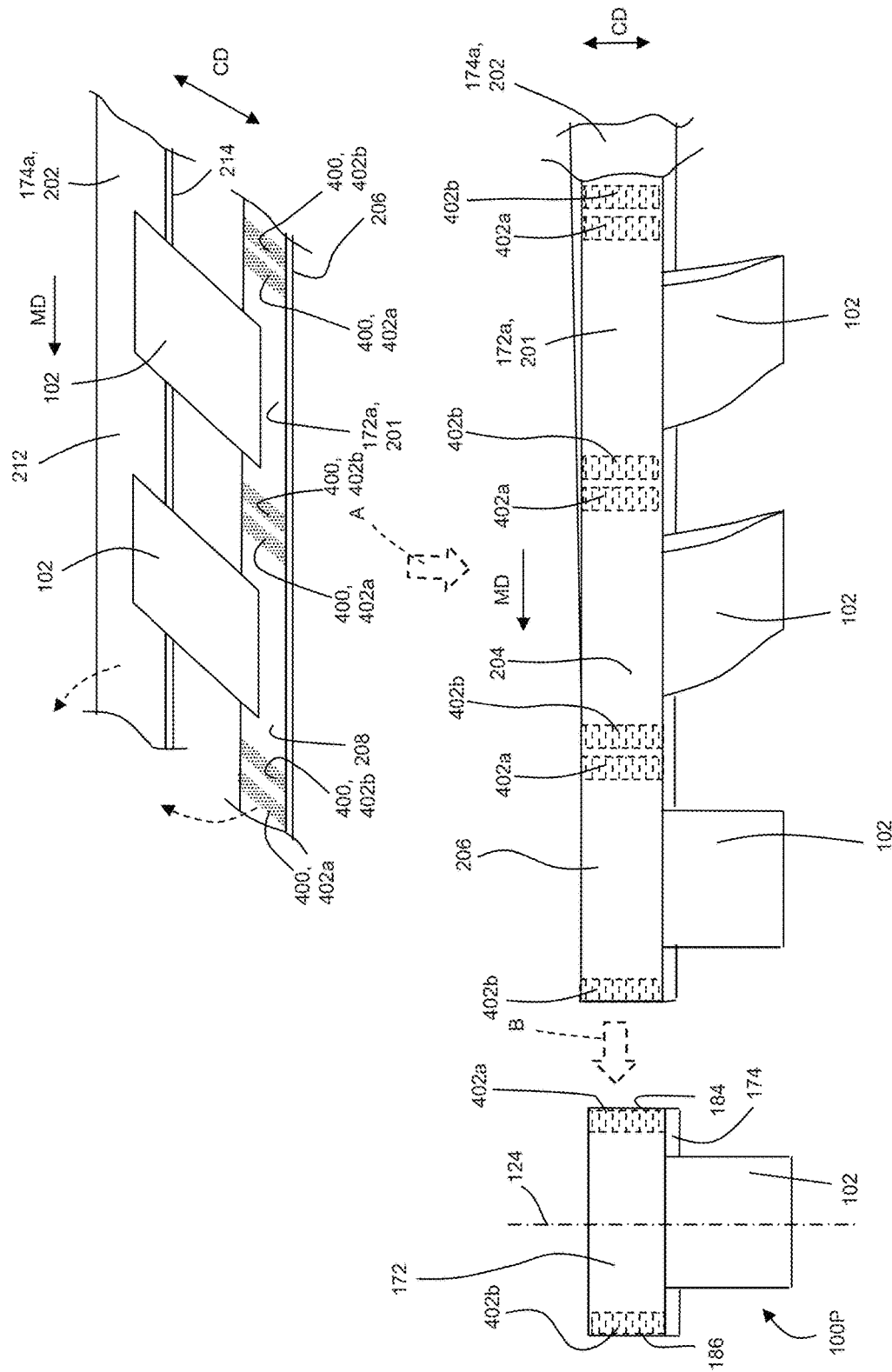
FIG. 8A is a schematic illustration of a second diaper pant assembly process with elastomeric laminates.

With continued reference to FIG. 8, during subsequent assembly operations, the chassis 102 may be folded (represented by the dashed arrow "A") so as to position the second surface 208 of the first substrate 201 into a facing relationship with the first surface 212 of the second substrate 202. Pressure may also be applied to the first substrate 201 and the second substrate 202 in the adherence zones 402 to help the tackifier free adhesive 400 to penetrate into and/or bond the first and second substrates 201, 202 together to form a laminate 204. Subsequently, discrete diaper pants 100P may be formed by separating the first and second substrates 201, 202 into first and second belts 172, 174 by cutting along the cross direction CD through the adherence zones 402. As such, the adherence zones 402 may be divided to define first and second adherence zones 402*a*, 402*b* that may correspond with first and second side seams 184, 186, respectively. It is to be appreciated that instead of having an adherence zone 402 that is subsequently divided into first and second adherence zones 402*a*, 402*b*, the tackifier free adhesive 400 may be applied so as to define the discrete first and second adherence zones 402*a*, 402*b*, such as shown for example in FIG. 8A. As such, the first and second substrates 201, 202 cut along the cross direction CD between the first and second adherence zones 402*a*, 402*b*. It is also to be appreciated that the tackifier free adhesive 400 may be applied to either or both the first and second substrates 201, 202.

Figure 10:
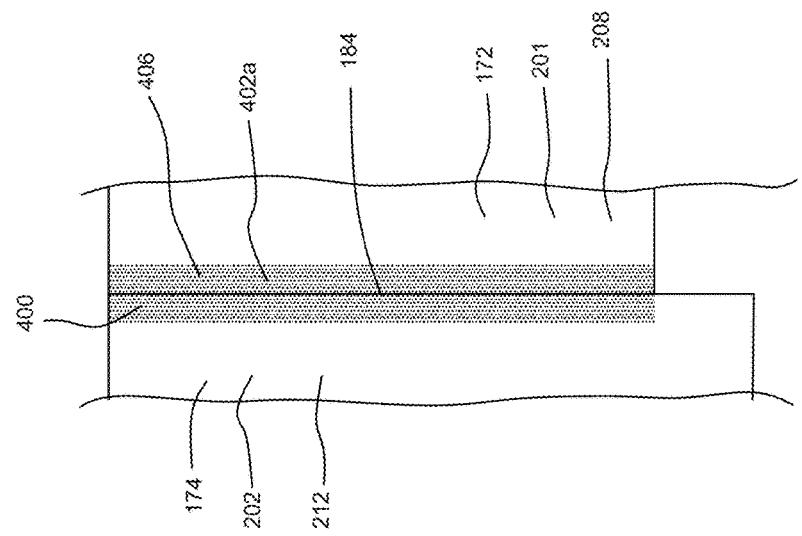
FIG. 10 is a side view of the side seam taken along the sectional line 10-10 of FIG. 9.
Figure 9:
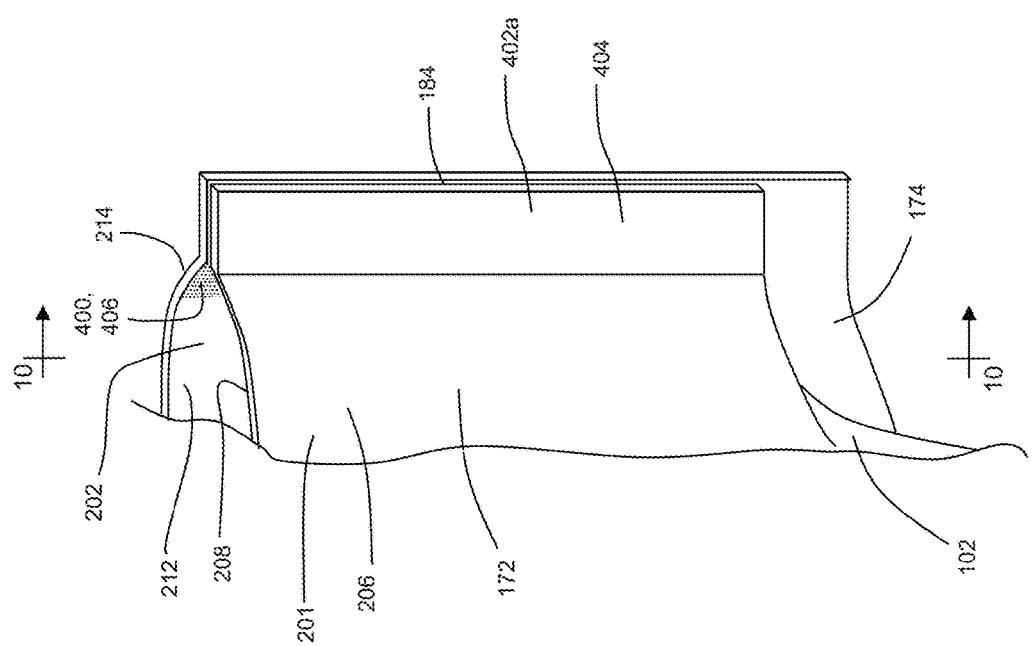
FIG. 9 is a detailed view of a side seam.

Referring now to FIGS. 8, 9, and 10, at the side seams 184, 186, the first substrate 201 may be bonded with the second substrate 202 to define a first region 404 and a second region 406 of the adherence zones 402*a*, 402*b*. FIGS. 9 and 10 show detailed views of the first side 184, which may be a mirror image of the second side seam 186. As shown in FIGS. 9 and 10, in the first region 404 of the adherence zone 402*a*, the tackifier free adhesive 400 is positioned between and bonds the second surface 208 of the first substrate 201 with the first surface 212 of the second substrate 202. And in the second region 406 of the adherence zone 402, the tackifier free adhesive 400 is positioned between and does not bond the second surface 208 of the first substrate 201 with the first surface 212 of the second substrate 202. During subsequent processing operations, such as folding and packaging, the tackifier free adhesive 400 in the second region 406 may not act to unintentionally bond with other components of the diaper pant 100P. In addition, the tackifier free adhesive 400 in the second region 406 may also be exposed to a wearer's skin and/or clothing during use of the article without unintentionally bonding to the wearer's skin and/or clothing.

It is to be appreciated that side seams may be formed with the methods and apparatuses herein with tackifier free adhesive only, and may also be formed in conjunction with mechanical bonding processes. It also to be appreciated that the methods and apparatuses herein may be adapted to operate with various types of absorbent article assembly processes, such as disclosed for example in U.S. Pat. Nos. 8,186,296; 9,265,672; 9,248,054; and 9,730,839 and U.S. Patent Publication Nos. 2013/0255861 A1; 2013/0255862 A1; 2013/0255863 A1; 2013/0255864 A1; and 2013/0255865 A1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of bonding substrates, the method comprising:
providing a first substrate comprising a first surface and an opposing second surface;
providing a second substrate comprising a first surface and an opposing second surface;
heating a tackifier free adhesive;
subsequent to heating, applying the tackifier free adhesive to the first surface of the second substrate to define an adherence zone;
positioning the first substrate on the adherence zone of the second substrate to define a first region of the adherence zone wherein the tackifier free adhesive is positioned between the second surface of the first substrate and the first surface of the second substrate, and a second region of the adherence zone wherein the tackifier free adhesive is not positioned between the second surface of the first substrate and the first surface of the second substrate; and
pressing the first substrate and the second substrate against each other;
removing heat energy from the second region of the adherence zone;

folding the second substrate to position a portion of the first surface of the second substrate into direct contact with the first surface of the first substrate and the second region of the adherence zone, wherein folding is performed subsequent to removing heat energy.

2. The method of claim 1, wherein the second surface of the first substrate comprises a first area, and wherein the adherence zone comprises a second area, wherein the second area is equal to or greater than the first area.

3. The method of claim 1, wherein removing heat energy further comprises forcing air across the first surface of the second substrate.

4. The method of claim 1, wherein the portion of the first surface of the second substrate in direct contact with the first surface of the first substrate and the second region of the adherence zone does not adhere to the second region of the adherence zone.

5. The method of claim 1, wherein the first substrate comprises a first nonwoven and the second substrate comprises a second nonwoven.

6. The method of claim 5, wherein pressing further comprises forcing the tackifier free adhesive into the first substrate and the second substrate.

7. The method of claim 1, wherein providing the first substrate further comprises cutting a discrete piece from a continuous first substrate.

8. The method of claim 7, wherein providing the second substrate further comprises advancing a continuous second substrate in a machine direction.

9. The method of claim 1, further comprising converting the first substrate and the second substrate into components of an absorbent article.

10. The method of claim 9, wherein the first substrate comprises one of a waist band, a connection zone, a leg cuff, an absorbent chassis, a first elastic belt and wherein the second substrate comprises one of a topsheet, a backsheet, and a second elastic belt.

11. A method for making a laminate, the method comprising:
providing a discrete first substrate comprising a first surface and an opposing second surface, the discrete first substrate further comprising a first area;
advancing a continuous second substrate comprising a first surface and an opposing second surface;
heating a tackifier free adhesive;
subsequent to heating, applying the tackifier free adhesive to the first surface of the continuous substrate to define an adherence zone comprising a second area, wherein the second area is greater than the first area;
forming a laminate by positioning the discrete first substrate on the adherence zone on the continuous second substrate to define a first region of the adherence zone wherein the tackifier free adhesive is positioned between the second surface of the first substrate and the first surface of the second substrate, and a second region of the adherence zone wherein the tackifier free adhesive is not positioned between the second surface of the first substrate and the first surface of the second substrate;
pressing the discrete first substrate and the continuous second substrate against each other to force the tackifier free adhesive into the first substrate and the second substrate;
cutting the laminate into discrete parts;
folding at least one of the discrete parts to position a portion of the first surface of the second substrate into direct contact with the first surface of the first substrate and the second region of the adherence zone; and
converting the first substrate and the second substrate into components of an absorbent article;
wherein the first substrate comprises one of a waist band, a connection zone, a leg cuff, an absorbent chassis, and a first elastic belt and wherein the second substrate comprises one of a topsheet, a backsheet, and a second elastic belt.

12. The method of claim 11, further comprising removing heat energy from the second region of the adherence zone.

13. The method of claim 11, the portion of the first surface of the second substrate in direct contact with the first surface of the first substrate and the second region of the adherence zone does not adhere to the second region of the adherence zone.

* * * * *